United States Patent
Hibri et al.

(10) Patent No.: US 10,786,360 B2
(45) Date of Patent: Sep. 29, 2020

(54) PERCUTANEOUS IMPLANTABLE NUCLEAR PROSTHESIS

(71) Applicant: Spinal Stabilization Technologies LLC, San Antonio, TX (US)

(72) Inventors: Nadi S. Hibri, San Antonio, TX (US); W. Loren Francis, San Antonio, TX (US); Mark A. Novotny, San Antonio, TX (US)

(73) Assignee: SPINAL STABILIZATION TECHNOLOGIES LLC, San Antonio, TX (US)

( * ) Notice: Subject to any disclaimer, the term of this patent is extended or adjusted under 35 U.S.C. 154(b) by 1232 days.

(21) Appl. No.: 14/932,366

(22) Filed: Nov. 4, 2015

(65) Prior Publication Data

US 2016/0120654 A1    May 5, 2016

Related U.S. Application Data

(60) Provisional application No. 62/074,873, filed on Nov. 4, 2014.

(51) Int. Cl.
| | | |
|---|---|---|
| A61F 2/44 | (2006.01) | |
| A61F 2/46 | (2006.01) | |
| A61F 2/30 | (2006.01) | |

(52) U.S. Cl.
CPC ............. *A61F 2/441* (2013.01); *A61F 2/442* (2013.01); *A61F 2/4611* (2013.01);
(Continued)

(58) Field of Classification Search
CPC .... A61F 2/441; A61F 2/442; A61F 2002/302; A61F 2002/30581; A61F 2002/30583;
(Continued)

(56) References Cited

U.S. PATENT DOCUMENTS

| 4,187,390 A | 2/1980 | Gore .................... 174/102 R |
| 4,478,898 A | 10/1984 | Kato .................... 428/36.91 |

(Continued)

FOREIGN PATENT DOCUMENTS

| CN | 101076302 A | 11/2007 |
| CN | 101557779 A | 10/2009 |
| WO | WO 2006/130796 | 12/2006 |

OTHER PUBLICATIONS

Supplementary European Search Report issued in European Application No. 15857214.9, dated Oct. 10, 2017.
(Continued)

*Primary Examiner* — David W Bates
*Assistant Examiner* — Marcela I Shirsat
(74) *Attorney, Agent, or Firm* — Norton Rose Fulbright

(57) ABSTRACT

A prosthesis for implantation in a de-nucleated intervertebral disc includes a fiber ring-like layer which encloses a polymeric layer to create an annular space. The annular space is inflatable with an in-situ curable liquid polymer and forms an interior cavity. The annular space may be expanded uniformly or differentially to be tailored to the needs of a particular vertebral segment and to achieve optimal disc space width and angle, thereby stabilizing the segment while preserving normal motion of the vertebral segment. The interior cavity provides a void that allows inward deformation of the implant during weight bearing activities and bending. The prosthesis can be elastically deformed through axial elongation to a reduced profile to load into a delivery cannula using pulling techniques.

20 Claims, 12 Drawing Sheets

(52) U.S. Cl.
CPC ....... *A61F 2/3094* (2013.01); *A61F 2002/302* (2013.01); *A61F 2002/30581* (2013.01); *A61F 2002/30583* (2013.01); *A61F 2002/30586* (2013.01); *A61F 2002/30971* (2013.01); *A61F 2002/444* (2013.01); *A61F 2002/4495* (2013.01); *A61F 2002/4627* (2013.01)

(58) Field of Classification Search
CPC ...... A61F 2002/30586; A61F 2002/444; A61F 2002/4495
USPC ................................................... 623/17.12
See application file for complete search history.

(56) References Cited

U.S. PATENT DOCUMENTS

| | | | |
|---|---|---|---|
| 4,619,641 A | 10/1986 | Schanzer | 604/8 |
| 4,743,480 A | 5/1988 | Campbell et al. | 428/36.5 |
| 5,152,782 A | 10/1992 | Kowligi et al. | 623/1.46 |
| 5,192,310 A | 3/1993 | Herweck et al. | 623/1.27 |
| 5,466,509 A | 11/1995 | Kowligi et al. | 428/141 |
| 5,628,786 A | 5/1997 | Banas et al. | 623/1.13 |
| 5,827,327 A | 10/1998 | McHaney et al. | 623/1.44 |
| 5,860,425 A | 1/1999 | Benderev et al. | 128/898 |
| 5,865,845 A | 2/1999 | Thalgott | 623/17.16 |
| 5,879,366 A | 3/1999 | Shaw et al. | 606/213 |
| 5,888,226 A | 3/1999 | Rogozinski | 623/17.16 |
| 5,910,277 A | 6/1999 | Ishino et al. | 264/127 |
| 5,928,284 A | 7/1999 | Mehdizadeh | 623/17.13 |
| 5,935,147 A | 8/1999 | Kensey et al. | 606/213 |
| 5,954,767 A | 9/1999 | Pajotin et al. | 623/23.72 |
| 5,972,022 A | 10/1999 | Huxel | 606/215 |
| 5,976,174 A | 11/1999 | Ruiz | 606/213 |
| 6,001,125 A | 12/1999 | Golds et al. | 623/23.7 |
| 6,001,130 A | 12/1999 | Bryan et al. | 623/17.16 |
| 6,007,570 A | 12/1999 | Sharkey et al. | 607/96 |
| 6,007,575 A | 12/1999 | Samuels | 623/1.15 |
| 6,019,793 A | 2/2000 | Perren et al. | 623/17.16 |
| 6,036,724 A | 3/2000 | Lentz et al. | 623/1.1 |
| 6,126,682 A | 10/2000 | Sharkey et al. | 607/96 |
| 6,127,597 A * | 10/2000 | Beyar | A61B 17/7266 606/86 R |
| 6,140,452 A | 10/2000 | Felt et al. | 528/60 |
| 6,180,848 B1 | 1/2001 | Flament et al. | 623/11.11 |
| 6,206,921 B1 | 3/2001 | Guagliano et al. | 606/92 |
| 6,224,630 B1 | 5/2001 | Bao et al. | 623/17.16 |
| 6,344,054 B1 | 2/2002 | Parodi | 623/1.13 |
| 6,361,637 B2 | 3/2002 | Martin et al. | 156/187 |
| 6,398,803 B1 | 6/2002 | Layne et al. | 623/1.13 |
| 6,402,750 B1 | 6/2002 | Atkinson et al. | 606/279 |
| 6,419,704 B1 | 7/2002 | Ferree | 623/17.12 |
| 6,428,576 B1 | 8/2002 | Haldimann | 623/17.16 |
| 6,436,143 B1 | 8/2002 | Ross et al. | 623/17.16 |
| 6,673,103 B1 | 1/2004 | Golds et al. | 623/1.13 |
| 6,733,533 B1 | 5/2004 | Lozier | 623/17.12 |
| 6,780,497 B1 | 8/2004 | Walter | 428/311.51 |
| 6,852,223 B2 | 2/2005 | Huang et al. | 210/500.36 |
| 6,893,466 B2 | 5/2005 | Trieu | 623/17.16 |
| 7,156,877 B2 | 1/2007 | Lotz et al. | 623/17.16 |
| 7,273,497 B2 | 9/2007 | Ferree | 623/17.16 |
| 7,297,158 B2 | 11/2007 | Jensen | 623/1.44 |
| 7,632,291 B2 | 12/2009 | Stephens et al. | 606/195 |
| 8,419,839 B2 | 4/2013 | Shimatani | 96/12 |
| 8,449,660 B2 | 5/2013 | Shimatani et al. | 96/11 |
| 8,979,931 B2 | 3/2015 | Stad et al. | 623/17.12 |
| 2002/0198588 A1 | 12/2002 | Armstrong et al. | 623/1.13 |
| 2003/0028251 A1 | 2/2003 | Mathews | 623/17.16 |
| 2003/0040772 A1 | 2/2003 | Hyodoh et al. | 606/200 |
| 2003/0114917 A1 | 6/2003 | Holloway et al. | 623/1.13 |
| 2005/0015150 A1 | 1/2005 | Lee | 623/17.12 |
| 2005/0065609 A1 | 3/2005 | Wardlaw | 623/17.12 |
| 2005/0090901 A1 | 4/2005 | Studer | |
| 2005/0137675 A1 | 6/2005 | Dubson et al. | 623/1.4 |
| 2006/0265077 A1 | 11/2006 | Zwirkoski | |
| 2007/0162135 A1 * | 7/2007 | Segal | A61F 2/441 623/17.11 |
| 2008/0119943 A1 | 5/2008 | Armstrong et al. | 623/23.7 |
| 2009/0082870 A1 | 3/2009 | Osman | |
| 2009/0112323 A1 | 4/2009 | Hestad et al. | |
| 2009/0163994 A1 | 6/2009 | Quigley et al. | 623/1.15 |
| 2010/0193999 A1 | 8/2010 | Anneaux et al. | 264/438 |
| 2010/0256766 A1 * | 10/2010 | Hibri | A61F 2/441 623/17.16 |
| 2014/0276832 A1 | 9/2014 | Hibri et al. | 606/79 |
| 2014/0277467 A1 | 9/2014 | Hibri et al. | 623/17.12 |
| 2017/0277467 A1 | 9/2017 | Daloze et al. | 623/17.12 |

OTHER PUBLICATIONS

International Search Report and Written Opinion for PCT/US2015/059011, dated Feb. 15, 2016.

The First Office Action from the China National Intellectual Property Administration issued in corresponding Patent Application No. 201680058105X dated Apr. 30, 2020.

Search Report from the China National Intellectual Property Administration issued in corresponding Patent Application No. 201680058105X dated Apr. 23, 2020.

Examination Report No. 1 from IP Australia issued in corresponding Patent Application No. 2016315964 dated May 23, 2020.

* cited by examiner

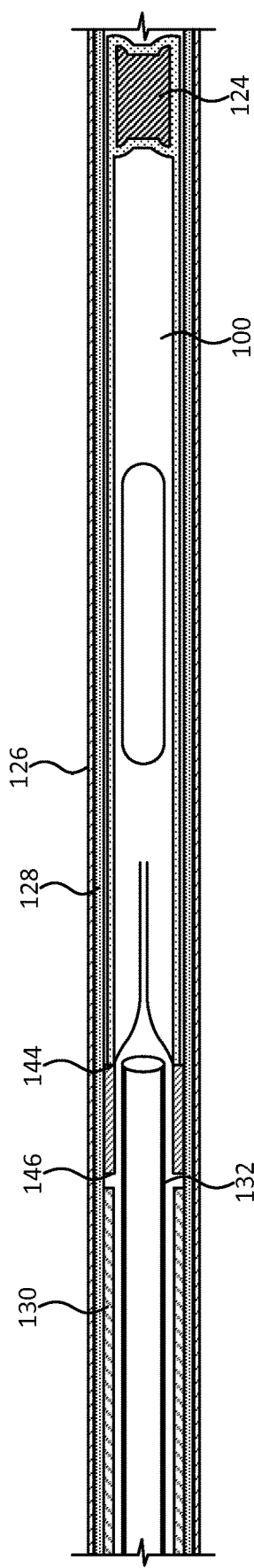
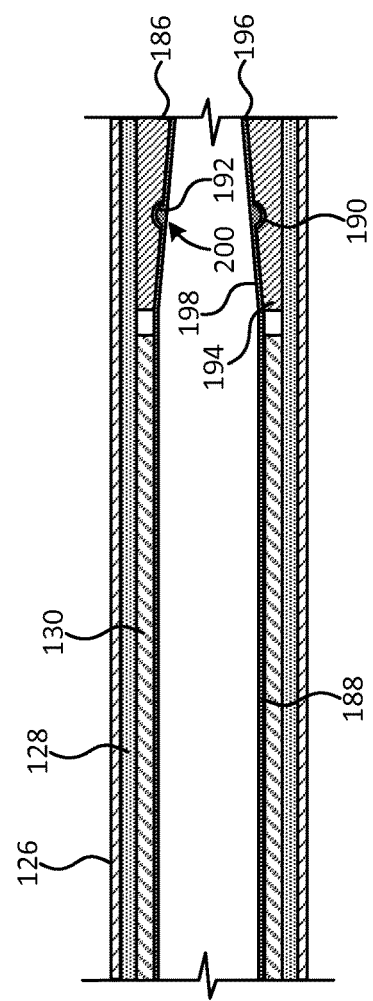

PERCUTANEOUS IMPLANTABLE NUCLEAR PROSTHESIS

CROSS-REFERENCE TO RELATED APPLICATIONS

This application claims the benefit of priority of U.S. Provisional Patent Application No. 62/074,873, filed Nov. 4, 2014, which is hereby incorporated by reference in its entirety.

BACKGROUND

1. Field of the Invention

This application relates generally to methods and devices for repairing an intervertebral disc. More specifically, the application relates to percutaneously deployed implantable spinal discs and methods for manufacturing and deploying such discs.

2. Description of Related Art

A common medical issue is back pain due to spinal disc injuries caused by trauma, the aging process or other disorders. One method of treatment that has been proposed is to remove the existing nucleus pulposus and replace it with a nuclear prosthesis (i.e., an artificial spinal disk) which is formed in situ using open surgery or minimally invasive surgical techniques.

Prior artificial disc technology has generally employed two types of implants. One type is a total disc designed as a substitute for the entire disc including the nucleus pulposus, the annulus fibrosus, and the vertebral end plates. The second type is a nuclear implant in which the annulus fibrosus and the end-plates are preserved. The shell formed by the annulus fibrosus itself has been used as an envelope to contain a curable biomaterial which is delivered to the cavity formed after a nucleotomy. Alternatively, an additional membrane may be provided inside the annulus fibrosus to form a shell to contain the biomaterial. Some prior art devices use two separate compartments or two nested balloons (a balloon placed within a balloon), which are filled in-situ with materials that have different hardnesses when cured, to simulate a natural disc.

In addition to artificial discs, a variety of systems have been disclosed that immobilize the spinal segment, namely prostheses designed and intended for intervertebral disc fusion. The various systems include the placement of cages, distendable sacks, fusion grafts, interbody fusion rings, fiber bags and cushions and constraining jackets. These fusion devices employ different techniques than disc replacement systems. Typically, these grafts are porous and they may be rigid or non-rigid. Hardenable and load-bearing materials are introduced and constrained by these structures to stabilize and fuse adjacent vertebrae.

Various techniques have been proposed for disc space distraction, including mechanical and hydrostatic techniques. For example, some techniques utilize pressurized injection of a biomaterial inside inflatable balloons to separate adjacent vertebra.

The existing techniques for forming a nuclear prosthesis in situ have not achieved convincing clinical acceptance or commercial success for a variety of reasons, including intricate designs that present problems pertaining to manufacture, implantation, and performance after implantation. Some of the problems associated with previous devices, specifically those related to percutaneous or minimally invasive designs intended for nuclear replacement, include:

1. Existing devices do not provide an integrated system that provides access to the nucleus pulposus, a nuclear evacuation apparatus that can achieve total or subtotal nucleotomy, and a delivery apparatus for the nuclear implant.
2. Existing devices inadequately seal the inflation device to the balloon, which results in leakage of the injected material around the inflation device during pressurized inflation.
3. Existing devices use inadequate or unreliable valve systems for preventing the curable biomaterial from leaking out of the implant after inflation and prior to curing.
4. Existing devices use hard materials that are insufficiently deformable, elastic and/or compressible. For example, existing devices often use a non-compressible center bearing portion to resist migration or to provide a more flexible region that more closely approximates the physical characteristics of the original nucleus. However, the vertebral end-plates are weakest in the center and strongest at the periphery. The use of a non-compressible center bearing portion increases risk of subsidence in the center. Furthermore, the lack of a central gas chamber or central void that provides a space for inward deformation of the annular portion may increase the risk of implant migration because of sudden or abnormal increase in pressure during loading or twisting.
5. Some existing devices attempt to construct an implant having a rigid outer portion with a more liquid but non-compressible interior. This design may work if the annulus is intact and can provide adequate elasticity. In reality, most patients who are candidates for disc replacement already have a damaged annulus, and this type of device functions poorly with a damaged annulus.
6. Existing devices provide inadequate nuclear evacuation, which causes problems such as eccentric placement, less than optimal peripheral placement with apposition of implant to inner annulus, less than optimal weight distribution to the peripheral end-plates, shifting of the implant and migration.
7. Inadequate closure of the annulotomy defect due to required surgical techniques. Existing techniques often involve cutting a flap through the annulus.
8. The materials used by existing devices are not durable and suffer from failure after usage.
9. Existing devices and techniques fail to restore and maintain sufficient disc space height to keep the spinal support ligaments taut.

Another issue with existing in situ formed prostheses is that it is very difficult to precisely control the force required to withdraw the inflation and pressurization cannula from the implant. If this force is too great, the implant may be dislodged through the annulotomy during detachment of the cannula. If the force required to withdraw the cannula from the implant is too small, the cannula may become prematurely detached from the implant during pressurization. Furthermore, fluid may leak around the connection.

The disclosed implant system is directed to overcoming one or more of the problems set forth above and/or other problems of the prior art.

SUMMARY

It is an object of the present application to provide a novel intervertebral disc for replacing a nucleus pulposus.

It is another object of the present application to provide a method of forming a nuclear prosthesis out of conformable materials which are adaptable to miniaturization.

It is yet another object of the present application to provide a method of deforming a prosthesis to load it into a delivery cannula.

It is a further object of the present application to provide a method of inserting and deploying a prosthesis into an intervertebral disc utilizing minimally invasive surgery or percutaneously.

It is a still further object of the present application to provide a valve mechanism for preventing leakage of a curable material from an implanted prosthesis.

It is a yet further object of the present application to provide a device which prevents subsidence and migration.

It is yet another object of the present application to provide a fluid connector assembly which may provide a secure fluid seal during pressurization of the implant within the disc, while still allowing efficient disengagement from the implant and not becoming prematurely detached from the implant.

It is a yet further object of the present application to provide a simple, efficient, and repeatable manufacturing method.

Aspects of the present disclosure relate to an interbody spinal non-fusion implant adapted for percutaneous deployment, and methods and instruments for inserting and deploying such implants. In some exemplary embodiments, a nuclear prosthesis is formed of a hollow ring-like synthetic fiber graft which may be filled with a curable elastomer. A one-way valve may be incorporated into the graft to allow elastomer to be injected into the graft while preventing backflow. The valve may be left in place to cure with the curable elastomer.

In some embodiment, the implant has a hollow ring-like configuration that allows a generally circumferential increase in size. The expandable implant may be designed to expand symmetrically or asymmetrically to restore disc height and angulation. Asymmetric expansion allow for change in the degree of lordosis, lateral angulation, or degree of compliance, compressibility or elasticity of the implant according to patient needs. The implant parameters may be adjusted to tailor intervertebral axial spacing and angulation for a patient. For example, the expandability of the implant/graft walls may be altered, or the durometer of the curable elastomer may be altered.

The ring-like implant forms an empty space in its interior. The interior space serves as a buffer zone for inward deformation of the cured elastomer within the lumen of the ring-like fiber graft.

The nuclear implant offers degrees of motion similar to those afforded by the anatomical spinal disc. Further, the durable biocompatible materials and design features provide a long working life. The nuclear implant has similar weight bearing and hydraulic capabilities as the nucleus pulposus.

The cured elastomer within the fiber graft provides torsional and compression stability. Thus, regardless of how loads are applied, the vectors of forces are substantially redirected centrally toward the interior cavity. Further, the fabric graft limits outward movement in the radial direction to lower stress on the annulus fibrosus.

Inflation of the implant separates the vertebral bodies along the cranial-caudal axis. This stretches and tightens the fibers of the annulus fibrosus to stabilization the spinal motion segment. By stabilizing the vertebral segment, while avoiding fusion, the repetitive traumatic forces on the ligaments and facet joints are reduced, thus slowing down the degenerative process and the development of spinal stenosis. Furthermore, by avoiding spinal fusion, the graft curtails the possibility of development of adjacent segment disease.

An aspect of the present disclosure is to preserve normal motion and reverse or arrest the degenerative cascade leading to segmental instability. This will alleviate pain and preserve the structural stability of the annulus fibrosus, facet joints and other osseous structures and ligaments.

Embodiments of the present disclosure include an artificial nuclear implant comprising an annular fiber graft which is inflated with an in-situ curable elastomer to form an interior cavity that allows inward deformation of the elastomer.

In one exemplary embodiment, the annular implant occupies the peripheral aspect of an evacuated disc space and is opposed to the inner margin of the annulus fibrosus and to the end-plates of the adjacent upper and lower vertebral bodies. A fluid is delivered into a lumen of the annular implant to create pressure to expand the implant and distract the adjacent vertebrae. After the access, delivery and inflation devices are removed, the elastomeric material cures in-situ within the annular graft to maintain vertebral distraction. The implant shares weight bearing and stabilization functions with the intrinsic annulus, which has been weakened by degeneration, fissures, or tears. A goal of the implant is to restore normal anatomical intervertebral spacing and angle and stabilization of the vertebral segment, while preserving its normal range of biomechanical movement.

In one aspect of the present disclosure, an implantable prosthetic device comprises an annular tubular inflatable membrane having an inflation port; a tubular fiber graft enclosing the inflatable membrane; an inflation stem coupled to the inflation port for removably receiving an inflation stylet in a substantially leakproof manner; and a one way valve assembly in the inflation stem to allow fluid to be injected into the interior of the inflatable membrane, the one way valve assembly comprising a flutter-type or duckbill valve.

In another aspect of the present disclosure, an implantable prosthetic device comprises an annular tubular inflatable membrane having an inflation port and first and second open ends; a tubular fiber graft enclosing the inflatable membrane and having first and second open ends; a coupling member coupling the first and second open ends of the inflatable membrane and fiber graft; and a one way valve assembly coupled to the inflation port to allow fluid to be injected into the interior of the inflatable membrane, the one way valve assembly comprising a flutter-type or duckbill valve.

In a further aspect of the present disclosure, a kit for implanting an implantable prosthetic device comprises a delivery cannula having an internal lumen with an inner diameter; a graft comprising an annular inflatable ring with an inflation stem for communicating with an interior of the annular inflatable ring, wherein the inflation stem has a proximal end and an opposed distal end and has an outer diameter and an inner diameter, and wherein the inflation stem is disposed in the internal lumen of the delivery cannula; a release cannula slidably disposed in the delivery cannula, the release cannula having a distal portion configured to engage the proximal portion of the inflation port, and an inflation stylet with at least one internal lumen, the inflation stylet having a distal portion with an outer diameter configured to be releasably press fit into the inflation stem.

In yet another aspect of the present disclosure, a method of manufacturing an implant comprises forming a tubular elastomeric membrane with first and second open ends and an inflation port; enclosing the elastomeric membrane in a tubular fiber graft; and coupling the first and second open ends together.

In an additional aspect of the present disclosure, a method of forming a graft comprises providing an implant as described herein; deploying the implant into a disc cavity; inflating the implant with a curable material; and allowing the curable material to cure.

The term "coupled" is defined as connected, although not necessarily directly. The terms "a" and "an" are defined as one or more unless this disclosure explicitly requires otherwise. The terms "substantially," "approximately," and "about" are defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

A device, system, or component of either that is configured in a certain way is configured in at least that way, but it can also be configured in other ways than those specifically described.

Any embodiment of any of the systems and methods can consist of or consist essentially of—rather than comprise/include/contain/have—any of the described elements, features, and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF DRAWINGS

FIG. 10 is a sectional view of a delivery cannula with the implant of FIG. 1, prior to deployment;

FIG. 11 is a sectional view of an alternative embodiment of an inflation stylet;

DETAILED DESCRIPTION

Figure 1:
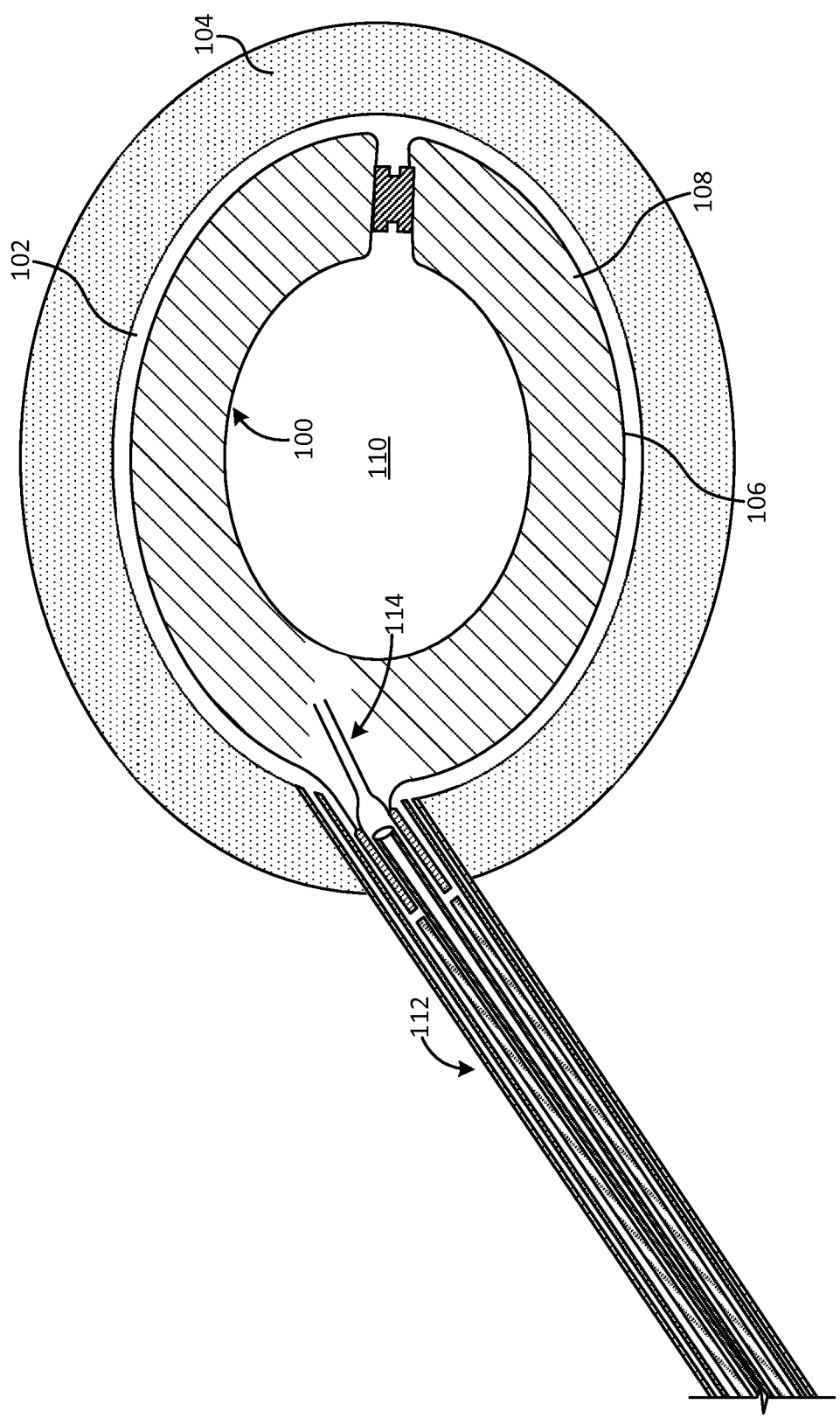
FIG. 1 is a sectional view of an implant according to an embodiment of the present disclosure after implantation into an intervertebral space.

In the following detailed description, reference is made to the accompanying drawings, in which are shown exemplary but non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims. In the accompanying drawings, like reference numerals refer to like parts throughout the various figures unless otherwise specified.

FIG. 1 illustrates an implant 100 in accordance with an exemplary embodiment of the present disclosure after deployment into a disc cavity 102. The disc cavity 102 is formed by performing a discectomy to remove the natural spinal disc. In some embodiments, the discectomy is performed using minimally invasive techniques, such as percutaneous techniques, so that the annulus fibrosus 104 is left substantially intact, with only a small access opening.

The implant 100 comprises an annular ring 106 which is filled with a curable elastomeric material 108, such as a curable silicone elastomer. The properties of material 108 may be selected to provide desired properties for the implant 100. For example, curing time, cured durometer, and other physical properties, such as elongation, tear, and tensile strength may be selected to provide implant 100 with desired characteristics.

Implant 100 forms a interior cavity 110 in the interior of annular ring 106. Interior cavity 110 allows annular ring 106 to deform inwardly to relieve stress and avoid placing excessive pressure on the central region of the vertebral end plates, as will be described in further detail below.

Annular ring 106 has an inflation port 114 with a one-way valve assembly 116 which allows curable material 108 to be introduced into annular ring 106 while it is still in a flowable state (i.e., prior to curing) while preventing curable material 108 from leaking out. In certain embodiments, annular ring 106 is formed by a tubular inflatable membrane 134 and a tubular fiber graft 136 which encloses the inflatable membrane 134.

Figure 2:
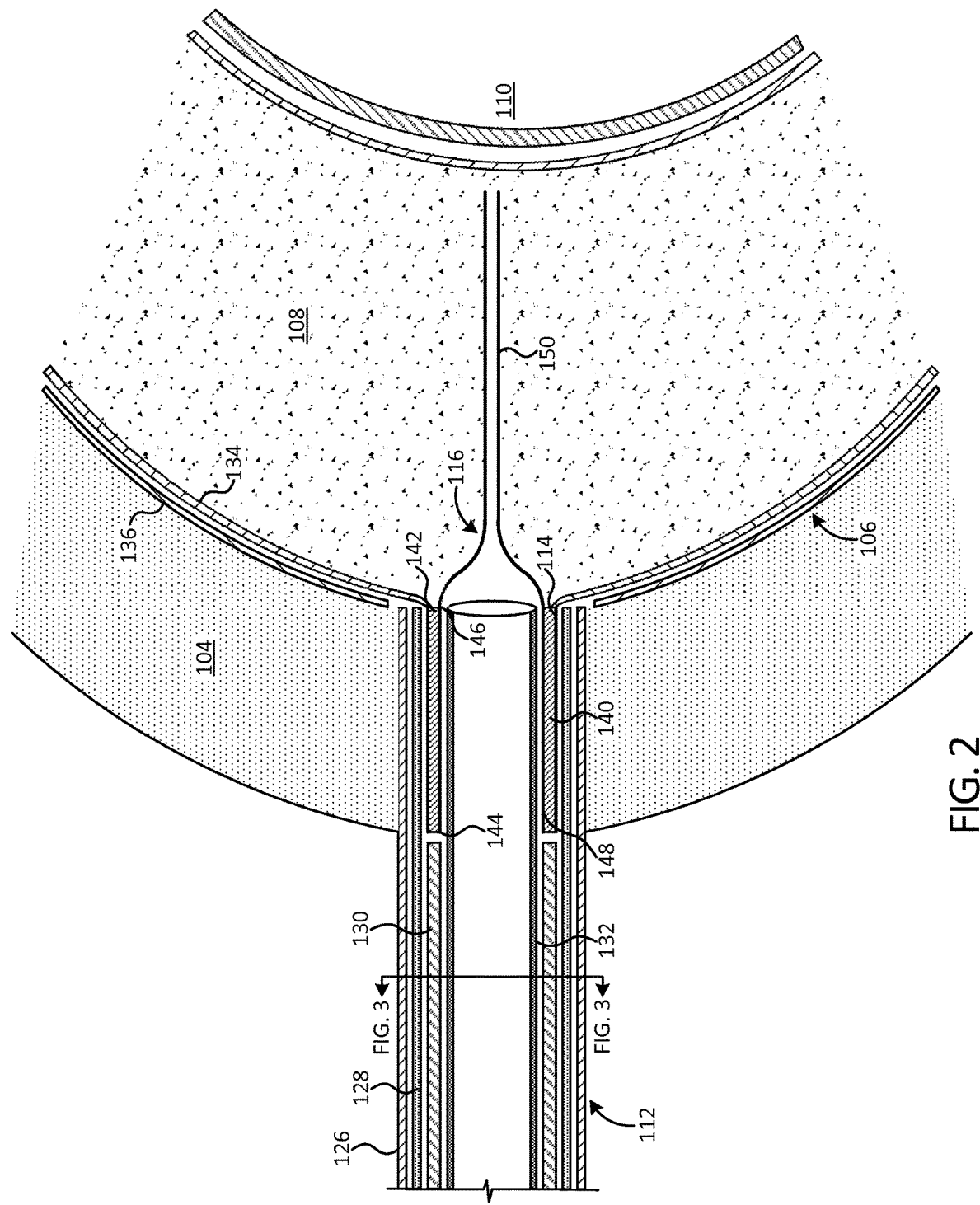
FIG. 2 is a sectional view of the inflation port and valve assembly of the implant of FIG. 1.
Figure 3:
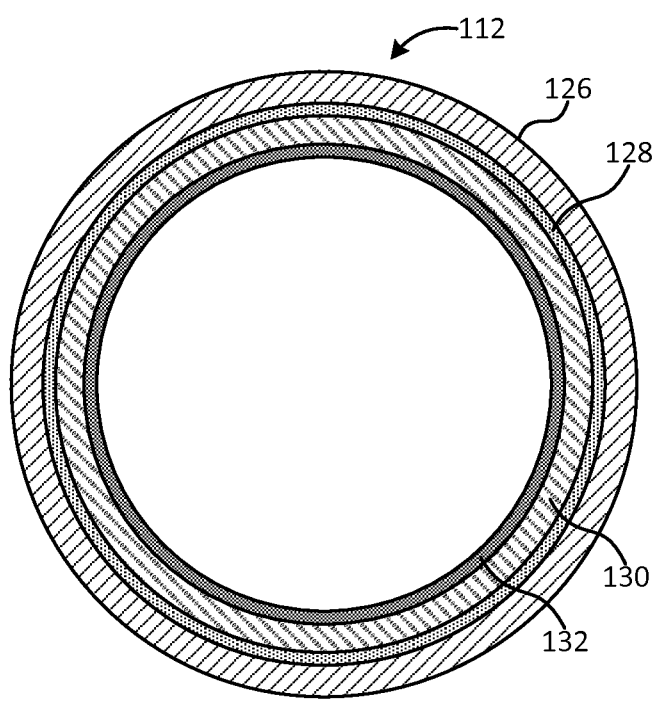
FIG. 3 is a sectional view taken along line 3-3 in FIG. 2.

Referring to FIG. 2, inflatable membrane 134 forms an annular balloon 138 with inflation port 114. A one-way valve assembly 140 is coupled to the inflation port 114. One-way valve assembly 140 allows curable material to be injected into annular balloon 138 while preventing substantially any material from escaping. In some embodiments, inflation port 114 comprises an inflation neck 208 which is formed integrally with inflatable membrane 134. In certain embodiments, an inflation stem 142 with a lumen 148 extending from a proximal end 144 to a distal end 146 is inserted into inflation neck 208 and coupled to inflation neck 208 by adhesive, welding, or the like. One way valve assembly 140 may comprise a duckbill valve (i.e., a flutter-type or Heimlich valve) 150 comprising a thin elastomeric material extending from inflation stem 142. The thin elastomeric material of duckbill valve 150 stretches to allow curable material 108 to flow through it when pressure is applied to curable material 108. When pressure is removed, the thin elastomeric material constricts to prevent back-flow. Duckbill valve 150 may be coupled to inflation stem 142 prior to assembly with inflatable membrane 134, or may be coupled to inflation stem 142 after inflation stem 142 is coupled to inflatable membrane 134. One-way valve assembly 140 and inflation stem 142 may be placed substantially in the inflation neck 208. That is, they may be placed so that they are outside of the annular portion of inflation membrane 134. Placing the inflation and valve componentry outside of the annular portion of inflation membrane 134 eases manufacturing, improves the function of implant 100 during deployment, and improves the functionality and durability of implant 100 after deployment.

In some embodiments, inflatable membrane 134 is formed of an elastic material, such as silicone, so that it is compliant (i.e., it expands as the internal pressure increases). A compliant balloon reduces the need for precise sizing of the membrane. In other embodiments, inflatable membrane 134 is semi-compliant. That is, inflatable membrane 134 expands to a given diameter under a certain amount of pressure, and only expands moderately from this diameter as the internal pressure increases beyond that pressure. Semi-compliant inflatable membranes 134 may be advantageous in some circumstances.

Figure 4:
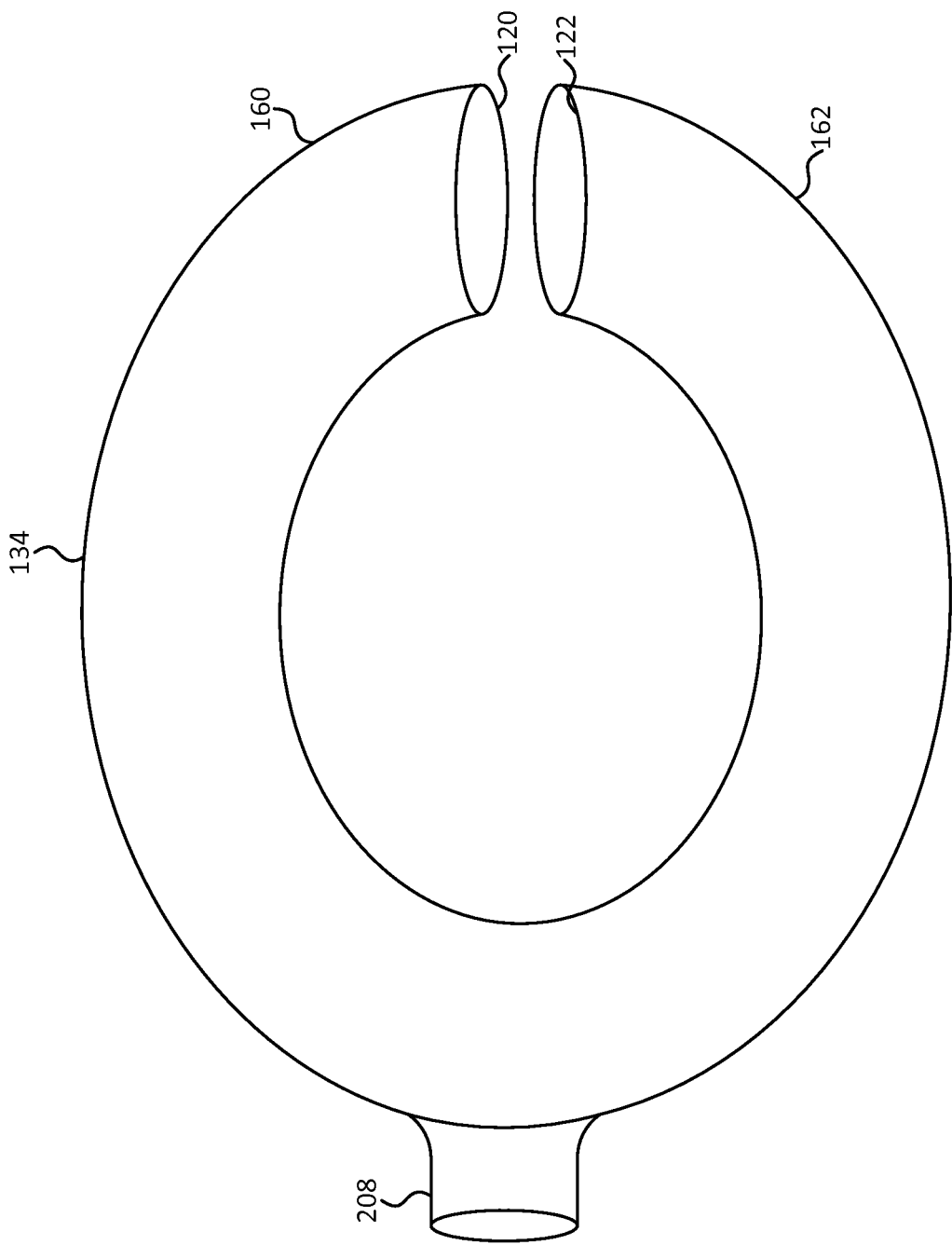
FIG. 4 is a plan view of an inflatable membrane of the implant of FIG. 1.
Figure 5:
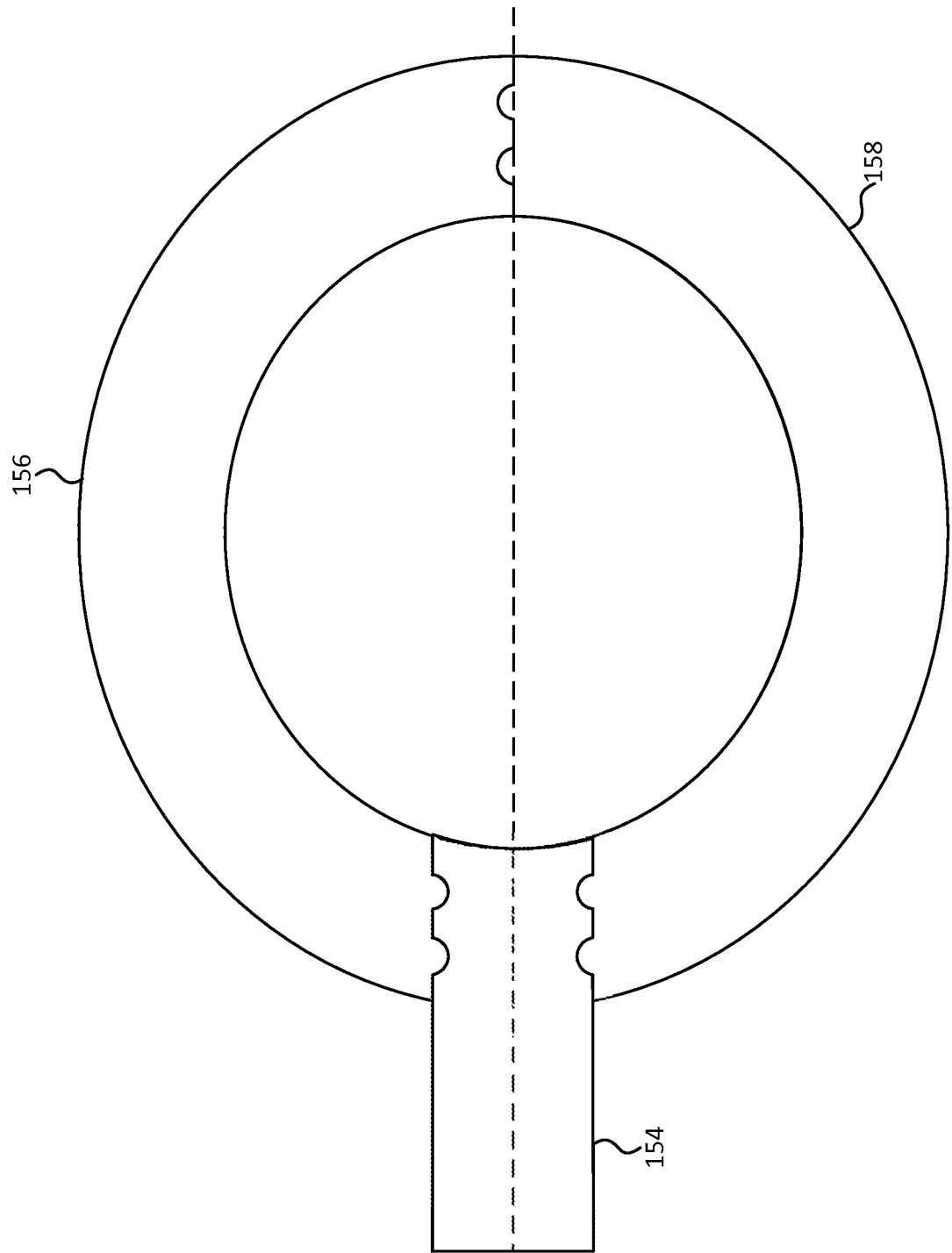
FIG. 5 is a plan view of a mandrel for making the inflatable membrane of the implant of FIG. 1.

Inflatable membrane 134 may be formed by conventional techniques, such as extrusion, injection molding or dip casting. In some embodiments, inflatable membrane 134 is formed by injection molding. Referring to FIGS. 4 and 5, a core mandrel 152 is used in conjunction with corresponding injection molding dies (not shown). In some embodiments, mandrel 152 comprises three pieces 154, 156, 158 which may be removably attached to one another by interlocking joints, such as threads or keys. Mandrel 152 is placed into the molding dies, and uncured silicone is injected into the die and allowed to cure to form inflatable membrane 134. After inflatable membrane 134 is cured, the molding dies are opened, and the mandrel with the inflatable membrane 134 is removed. The mandrel may then be removed through inflation port 114 and inflation neck 208. In some embodiments, mandrel pieces 154, 156 and 158 are disassembled and removed through inflation port 114 and inflation neck 208. In other embodiments, inflatable membrane 134 may be cut to form first and second legs 160, 162 with open ends 120, 122 through which mandrel pieces 156 and 158 are removed. In certain embodiments, first and second legs 160, 162 of inflatable membrane 134 are approximately the same length, although they may be unequal lengths.

Figure 7:
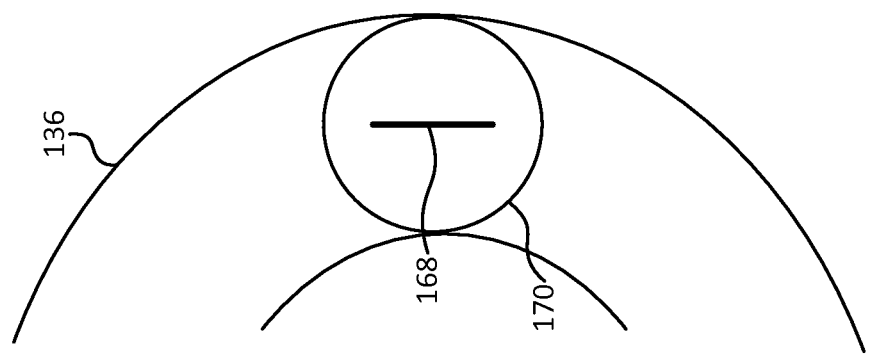
FIG. 7 is a plan view of an access opening in the tubular fiber graft of FIG. 6.
Figure 6:
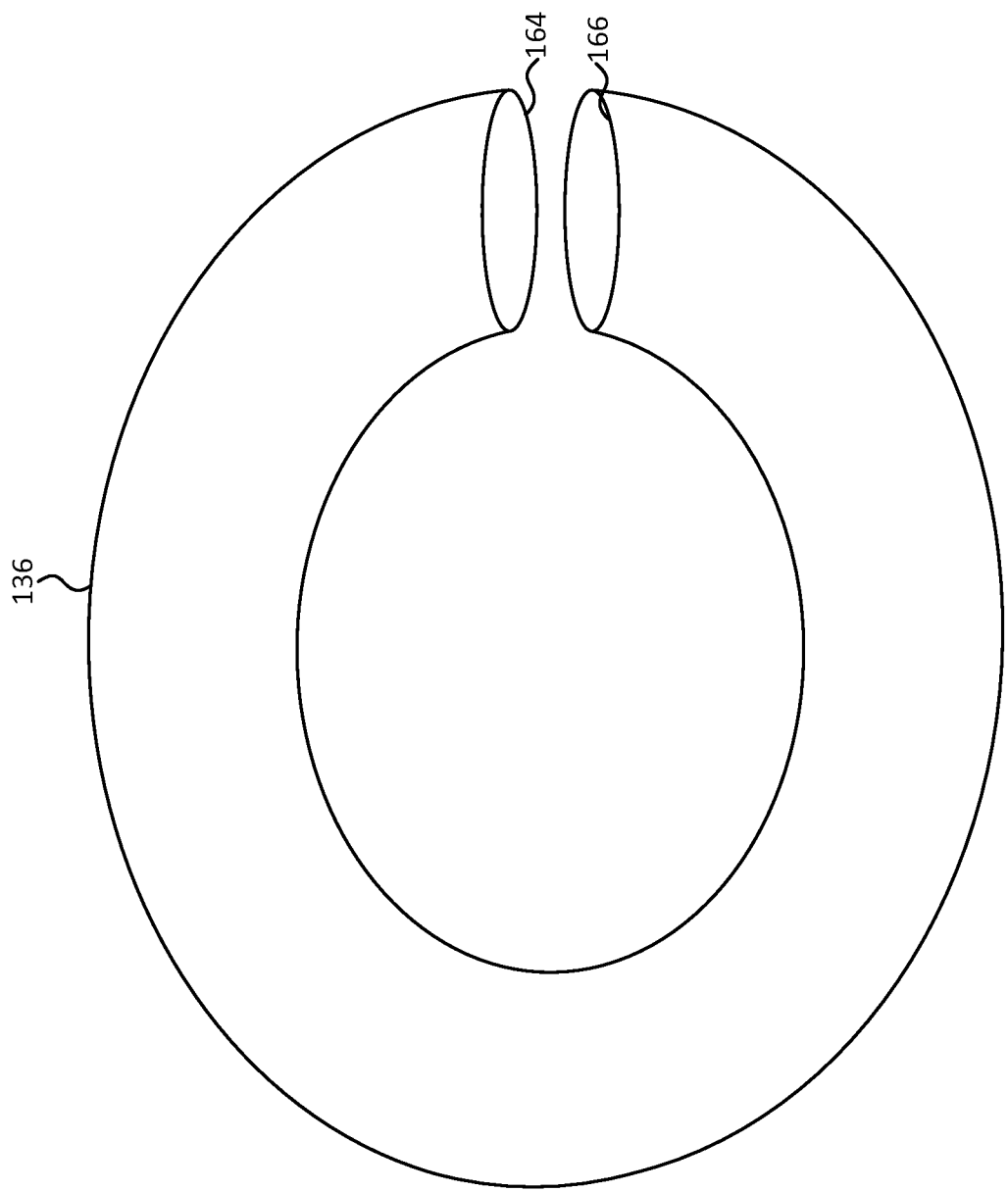
FIG. 6 is a plan view of a tubular fiber graft of the implant of FIG. 1.

Cutting inflatable membrane 134 to form legs 160, 162 allows tubular fiber graft 136 to be formed separately and then installed on inflatable membrane 134. Referring to FIGS. 6 and 7, in some embodiments, tubular fiber graft 136 comprises a textile formed of a biocompatible material. The textile material may be a woven, braided or knitted durable biocompatible material. In some embodiments, tubular graft 136 comprises a first layer comprising a plurality of semi-elastic or substantially inelastic fibers extending longitudinally and circumferentially along graft 136. In certain embodiments, a second layer of semi-compliant fibers are layered over the first layer. In other embodiments, circumferential fibers are formed from substantially inelastic materials, and hoop fibers are formed from semi-elastic materials. This allows the graft 100 to expand moderately in the cross-sectional plane while constraining radial or equatorial expansion. In this manner, graft 100 mostly deforms inward toward interior cavity 110 and in the axial or craniocaudal plane. In some embodiments, tubular fiber graft 136 incorporates radiopaque markers at one or more locations to enable clinicians to visualize graft 100 during implantation. In certain embodiments, the radiopaque markers comprise radiopaque fibers.

The cross-sectional diameter of tubular fiber graft 136 is selected to allow inflatable membrane 134 to be inflated to full size while preventing over-expansion of inflatable membrane 134. The materials are selected so that inflatable membrane 134 does not bond to fiber graft 136 and is free to move within fiber graft 136 to a limited extent.

In some embodiments, tubular fiber graft 136 is a split annular ring with first and second open ends 164, 166. An opening 168 is provided in tubular fiber graft 136 to provide access to inflation port 114. Opening 168 may be reinforced by stitching (e.g., a buttonhole stitch). Further, a reinforcing member 170 may be provided to reinforce the opening. Fiber graft 136 is installed over inflatable member 134 by placing inflatable member 134 through either first and second open end 164, 166 and threading it through fiber graft 136. Inflation neck 208 is placed through opening 168.

Figure 9:
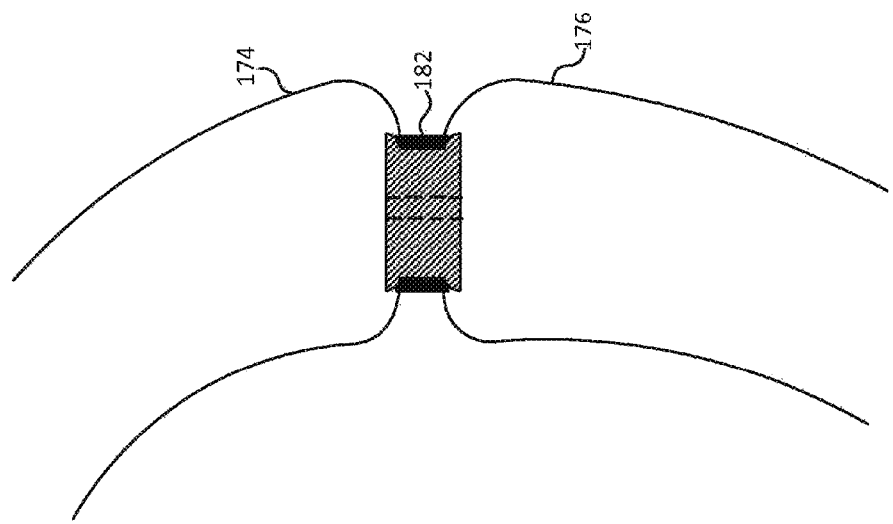
FIG. 9 is a partial sectional view of a portion of the implant of FIG. 1, after installation of a retaining member.
Figure 8:
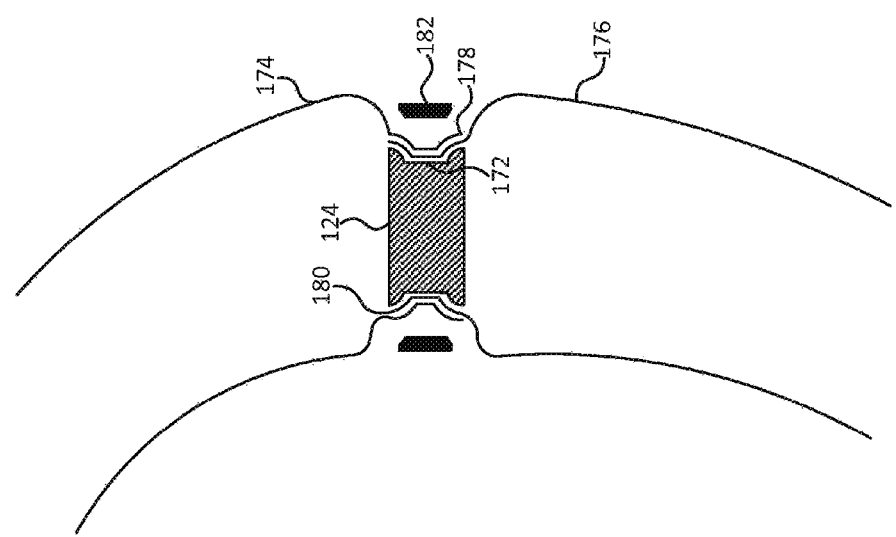
FIG. 8 is a partial sectional view of a portion of the implant of FIG. 1, prior to installation of a retaining member.

Open ends 164, 166 of fiber graft 136 and open ends 120, 122 of inflatable membrane 134 are coupled to one another to form implant annular ring 106. In one embodiment, a coupling member 124 is provided to couple open ends 164, 166 and open ends 120, 122. Referring to FIGS. 8 and 9, coupling member 124 comprises a cylindrical member with a groove 172. In FIGS. 8 and 9, inflatable member 134 and fiber graft 136 form first and second tubular legs 174, 176 with open distal ends 178, 180, respectively. For clarity, inflatable membrane 134 and fiber graft 136 are shown as a single line in FIGS. 8 and 9. Coupling member 124 is placed into the interior of open distal end 180 of second tubular leg 176, and open distal end 178 of first tubular leg 174 is placed over coupling member 124 and distal end 180 of second tubular leg 176. A retaining member 182 is placed over coupling member 124 to couple distal ends 178, 180 to coupling member 124. In some embodiments, retaining member 182 is a permanently crimpable member which is crimped into groove 172. Retaining member 182 may comprise a radiopaque material to serve as a radiopaque marker.

In some embodiments, coupling member 124 may be a solid member which forms a partition to prevent fluid communication between first and second tubular legs 174, 176. In other embodiments, coupling member may have a lumen which connects first and second tubular legs 174, 176.

FIG. 10 illustrates implant 100 loaded into percutaneous deployment device 112. Percutaneous deployment device 112 comprises a delivery cannula 128, a release cannula 130 and an inflation stylet 132. Deployment device 112 may be placed in an introducer or access cannula 126. Access cannula 126 extends through annulus fibrosus 104 to provide access to disc cavity 102. Access cannula 126 is deployed using conventional percutaneous access techniques. Access cannula 126 may be a conventional cannula. In some embodiments, access cannula 126 comprises an access cannula used to remove the nucleus pulposus, such as the access cannula described in US Patent Publication No. 2014/0276832, entitled "Surgical Device," which is hereby incorporated by reference in its entirety. Implant 100 is stretched out in a deflated state and placed into delivery cannula 128. The inner diameter of delivery cannula 128 is substantially the same as the outer diameter of inflation stem 142 so that inflation stem 142 fits snugly into delivery cannula 128. The outer diameter of release cannula 130 is selected to fit snugly into delivery cannula 128. The distal end 184 of release cannula 130 engages the proximal end 144 of inflation stem 142 so that release cannula 130 can be used to push inflation stem 142 and thus implant 100 out of the end of delivery cannula 128 to deploy implant 100 into disc cavity 106. Release cannula 130 can also be used to hold inflation stem 142 into place while withdrawing inflation stylet 132 after deployment (as will be described in further detail below).

Inflation stylet 132 is placed into inflation stem 142. Inflation stem 142 is elastic and stretched to fit over the outer diameter of inflation style 132 so that the two pieces fit together snugly. The snug fit of inflation stylet 132 into inflation stem 142 together with the snug fit of inflation stem 142 into delivery cannula 128 form a tight seal to substantially prevent leakage during deployment and inflation of implant 100. Furthermore, the snug fit prevents inadvertent dislodgment of the inflation stylet prior before completion of the inflation, despite the relatively high pressures which may be used to inflate inflatable membrane 134.

Referring to FIG. 11, in certain embodiments, inflation stem 186 is tapered from a proximal end 194 to a distal end 196. A distal end 198 of the inflation stylet 198 forms a complementary shape. A lock 200 releasably holds inflation stylet 198 in inflation stem 186. In certain embodiments, lock 200 comprises a protuberance 192 which engages a groove 190. In certain embodiments, protuberance 192 comprises a ridge molded around inflation stylet 198. The size, shape and number of ridges and grooves can be selected to provide a desired force required to detach the inflation stylet from the inflation stem.

Figure 12:
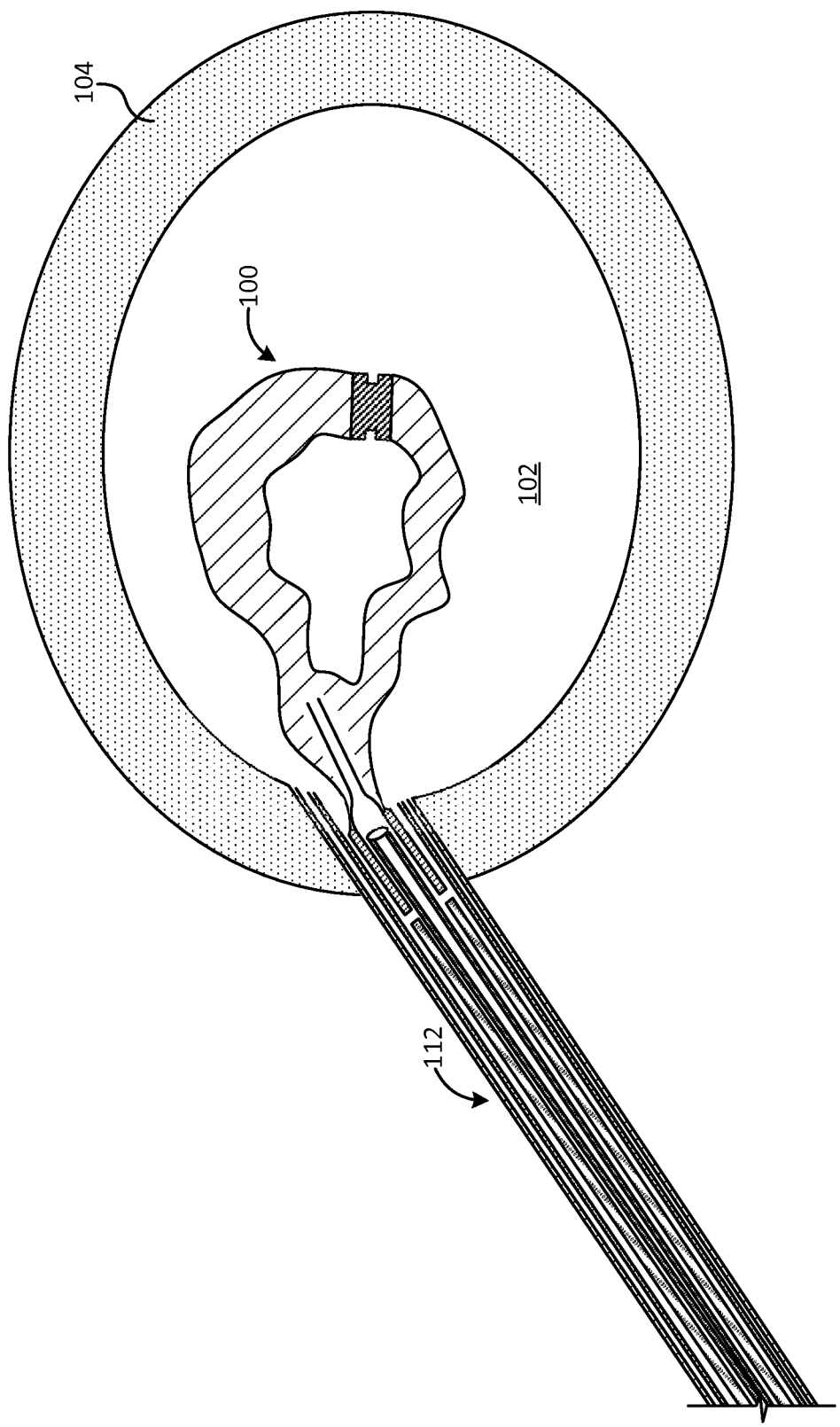
FIG. 12 is a sectional view of the implant of FIG. 1 which is partially implanted into the intervertebral space.

Referring to FIG. 12, to deploy implant 100, the existing nucleus pulposus at the target site is removed by inserting access cannula 126 through a small access opening through the annulus fibrosus 104. The existing nucleus pulposus is removed through access cannula 126 by performing a discectomy. The annulus fibrosus 104 is left substantially intact to form disc cavity 102.

Implant 100, which has been loaded into percutaneous deployment device 112, is inserted into the disc space. Release cannula 130 and inflation stylet 132 are pressed toward disc cavity 102 to engage proximal end 144 of inflation stem 142 and begin to deploy implant 100. In certain embodiments, a push member 210 extends from inflation stylet 132 and engages coupling member 124. During deployment, push member 210 pushes coupling member 124 toward the far end of the disc cavity 102 to help ensure proper placement of implant 100.

Alternatively, release cannula 130 may be advanced so that implant 100 is partially deployed, and curable material 108 may be delivered through inflation stylet 132 to partially inflate inflatable membrane 134. Release cannula 130 may then be advanced again, and additional curable material 108 may be delivered. This process is repeated until inflation stem 142 has been advanced to the distal end of delivery cannula 128, thereby fully deploying implant 100.

After implant 100 is fully deployed into disc cavity 102, curable 108 is deployed into the inflatable membrane 134 to press implant 100 firmly against annulus fibrosus 104 and distract adjacent vertebral segments. A pressurized syringe may be used to deploy curable material 108 and supply sufficient pressure achieve the desired intervertebral distraction. After sufficient curable material 108 is deployed, inflation stylet 132 may be removed. Release cannula 130 holds inflation stem 142 into place, thereby preventing inadvertent withdrawal of implant 100 when inflation style 132 is removed. One-way valve 116 prevents curable material 108 from leaking out of implant 100. Thus, inflation stylet 132 may be removed prior to curing of curable material 108. When inflation stylet 132 is removed, inflation stem 142, which is formed of an elastomeric material, collapses so that it only leaves a small amount of material in the opening of the annulus fibrosus (i.e., the annulotomy). The collapsed inflation stem 142 reinforces the function of duckbill valve 150 by preventing duckbill valve 150 from inverting due to the pressure of the curable material (prior to curing).

Curable material 108 may be a silicone elastomer. The properties of the material, such as the curing time, uncured viscosity, cured durometer, etc. may be selected as desired to provide the desired properties for graft 100, which are dependent upon the patient under treatment. The curable material 108 may be compatible with the material of inflatable membrane 134 so that they fuse together and form a single component.

Figure 13:
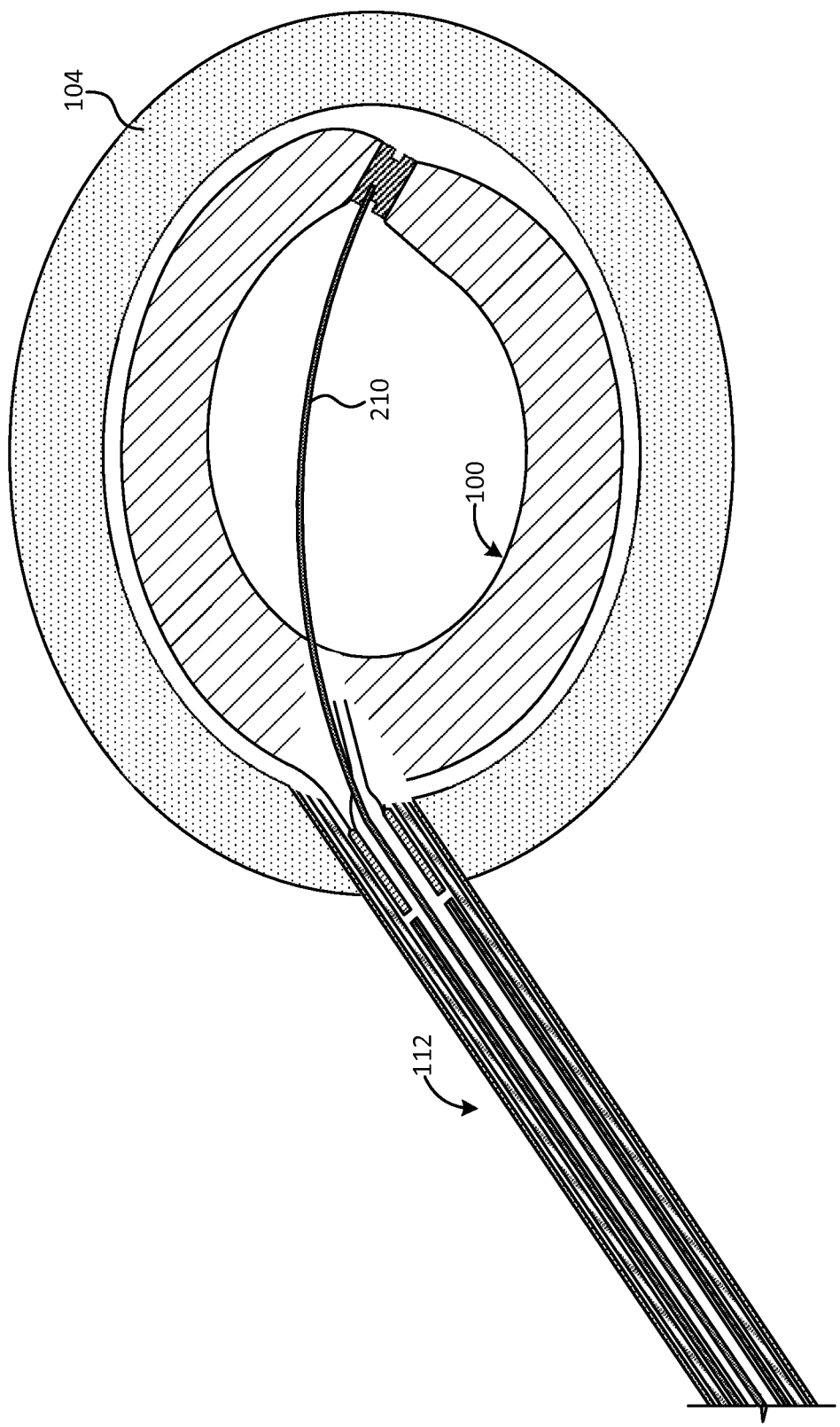
FIG. 13 is a sectional view of the implant of FIG. 1 which is partially implanted into the intervertebral space with a push member.
Figure 14:
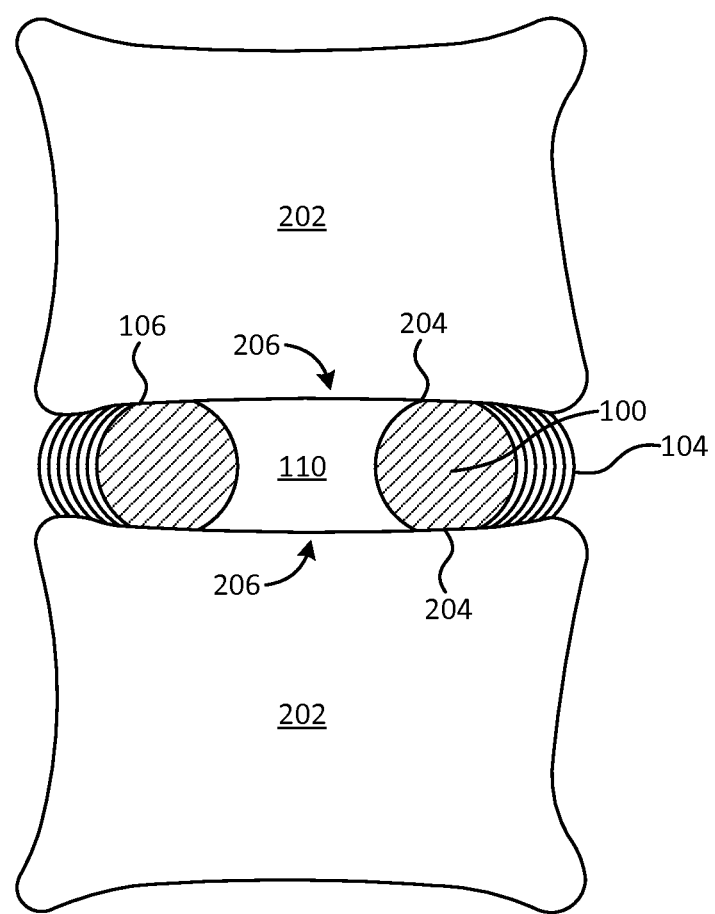
FIG. 14 is a diagrammatic view of an implanted implant of FIG. 1 with the adjacent vertebrae substantially aligned.
Figure 16:
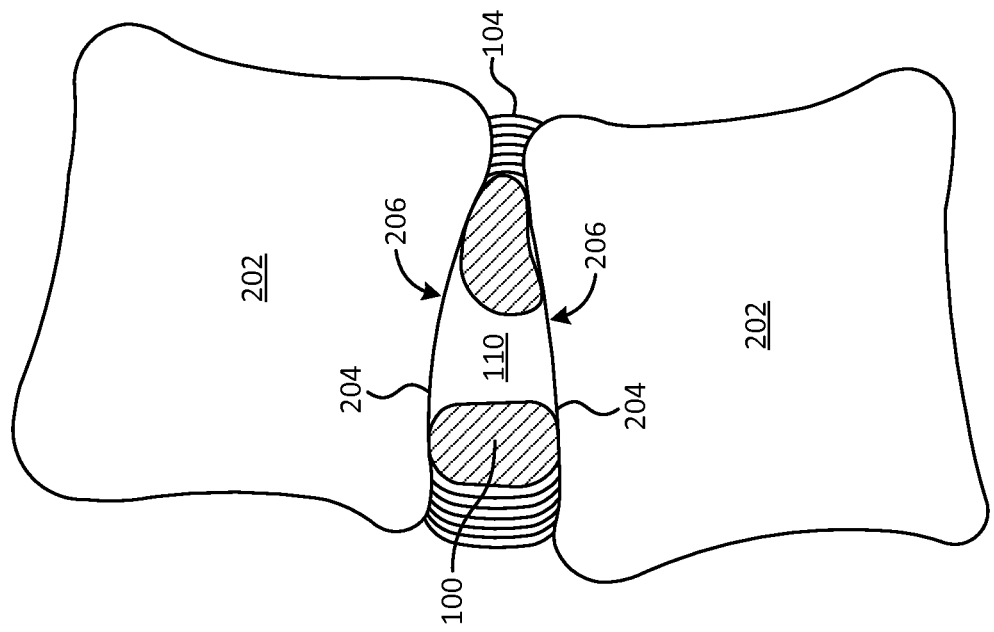
FIG. 16 is a diagrammatic view of an implanted implant of FIG. 1 with the adjacent vertebrae bent towards one another.
Figure 15:
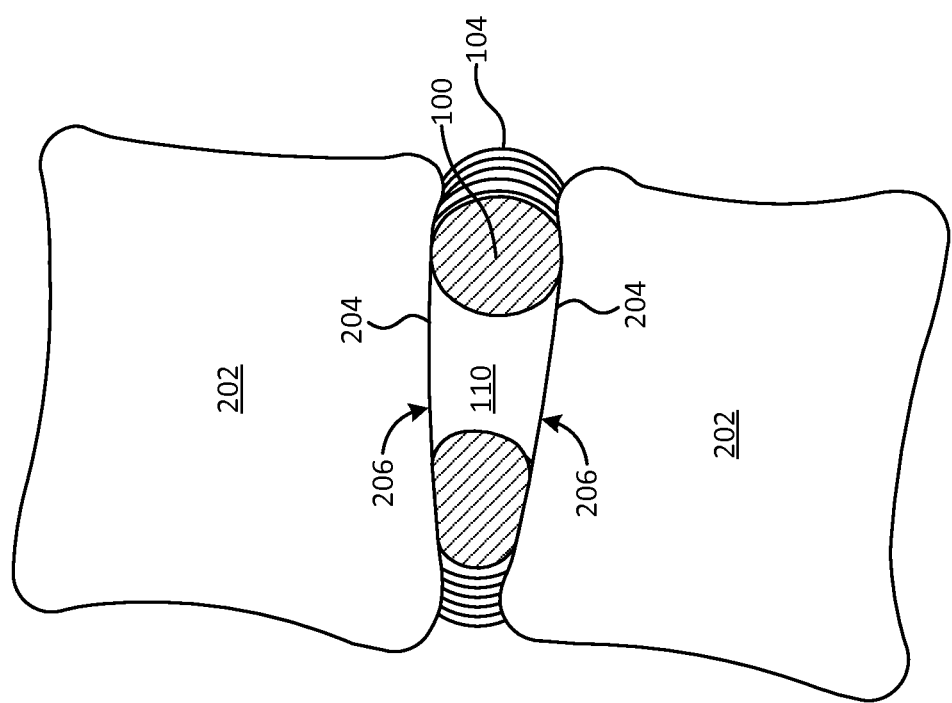
FIG. 15 is a diagrammatic view of an implanted implant of FIG. 1 with the adjacent vertebrae bent towards one another.

Referring to FIGS. 13-15, once implant 100 has cured, it forms a substantially non-compressible ring 106 which is contained within annulus fibrosus 104. Implant 100 distracts adjacent vertebral segments 202 by pressing against vertebral end plates 204. Interior cavity 110 is formed in the center of annular ring 106. When vertebral segments 202 are moved with respect to one another, annular ring 106 deforms into interior cavity 110. This prevents implant 100 from being subjected to too high of pressures, and prevents implant 100 from applying too high of pressures to vertebral end plates 204. Furthermore, the peripheral location of implant 100 distributes weight to the peripheral portions of the vertebral end plates, and interior cavity 110 prevents excessive force from being applied to the central region 206 of vertebral end plates 204. The peripheral portions of the end plate are typically stronger than the central regions. Further, interior cavity 110 provides space for shock absorption and for inward deformation during loading and sudden increases in intradiscal pressure.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted (e.g., threads may be substituted with press-fittings or welds). Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An implantable prosthetic device comprising:
   a) an annular hollow inflatable membrane having an inflation port, wherein the annular hollow inflatable membrane comprises a unitary, elastomeric member with a first open end and a second open end which are coupled together by a coupling member;
   b) a tubular fiber graft enclosing the inflatable membrane;
   c) a retaining member for coupling the annular hollow inflatable membrane and the tubular fiber graft to the coupling member;
   d) an inflation stem coupled to the inflation port for removably receiving an inflation stylet in a substantially leakproof manner; and
   e) a one way valve assembly in the inflation stem to allow fluid to be injected into an interior of the inflatable membrane, the one way valve assembly comprising a duckbill valve.

2. The implantable prosthetic device of claim 1, wherein the coupling member further comprises a lumen for fluidly connecting the first and second open ends of the annular hollow inflatable membrane.

3. The implantable prosthetic device of claim 1, wherein the inflation port further comprises an inflation neck extending from the annular hollow inflatable membrane.

4. The implantable prosthetic device of claim 3, wherein the inflation stem comprises a single lumen.

5. The implantable prosthetic device of claim 3, wherein the tubular fiber graft comprises an opening for receiving the inflation neck of the annular hollow inflatable membrane.

6. The implantable prosthetic device of claim 1, further comprising a deployment device comprising:
   a delivery cannula for receiving the inflatable membrane and tubular fiber graft in an uninflated state;
   a pushrod for moving the coupling member away from the inflation stem a towards a distal end of a disc cavity;
   an inflation stylet for delivering a curable material to the inflatable membrane; and
   a release cannula for allowing the inflation stylet to be removed without dislodging the inflatable membrane.

7. The implantable prosthetic device of claim 6, wherein the inner diameter of the delivery cannula and the outer diameter of the inflation stem are substantially the same, and wherein the graft comprises an annular inflatable graft that defines a hollow cavity when inflated.

8. The implantable prosthetic device of claim 1, wherein the coupling member comprises a lumen connecting the first and second open ends of the annular hollow inflatable membrane, and wherein the coupling member is opposite the inflation port when the annular hollow inflatable membrane is inflated.

9. An implantable prosthetic device comprising:
   a) an annular inflatable membrane having an inflation port and first and second open ends, the annular inflatable membrane comprising a unitary, elastomeric member;
   b) a tubular fiber graft enclosing the inflatable membrane and having first and second open ends;
   c) a coupling member coupling the first and second open ends of the inflatable membrane and fiber graft, wherein the coupling member comprises a lumen connecting the first and second open ends of the annular inflatable membrane, and wherein the coupling member is opposite the inflation port when the annular inflatable membrane is inflated; and
   d) a one way valve assembly coupled to the inflation port to allow fluid to be injected into an interior of the inflatable membrane, the one way valve assembly comprising a duckbill valve.

10. The implantable prosthetic device of claim 9, further comprising a retaining member for coupling the annular inflatable membrane and the tubular fiber graft to the coupling member.

11. The implantable prosthetic device of claim 9, further comprising an inflation stem detachably coupled to the inflation port for receiving an inflation stylet, wherein the coupling is substantially leakproof during inflation.

12. The implantable prosthetic device of claim 11, further comprising a locking device on the inflation stem configured to engage a mating locking device on the inflation stylet to prevent inadvertent dislodgement of the inflation stylet.

13. The implantable prosthetic device of claim 11, wherein the inflation stem is located outside of a chamber formed by the annular inflatable membrane.

14. The implantable prosthetic device of claim 11, wherein the inflation stem comprises a single lumen, and wherein the duckbill valve comprises a flutter valve.

15. The implantable prosthetic device of claim 11, further comprising an inflation stylet adapted to mate with the inflation stem.

16. The implantable prosthetic device of claim 9, wherein the inflatable membrane comprises an inflation neck extending from the inflation port.

17. The implantable prosthetic device of claim 16, wherein the tubular fiber graft comprises an opening for receiving the inflation neck of the inflatable membrane.

18. The implantable prosthetic device of claim 9, further comprising a deployment device comprising:
   a delivery cannula for receiving the inflatable membrane and tubular fiber graft in an uninflated state;
   an inflation stylet for delivering a curable material to the inflatable membrane; and
   a release cannula for allowing the inflation stylet to be removed without dislodging the inflatable membrane.

19. The implantable prosthetic device of claim 18, further comprising an inflation stem coupled to the inflation port wherein the inflation stem is configured to receive the inflation stylet and configured to be placed into the delivery cannula.

20. A kit for implanting an implantable prosthetic device, comprising:
   a) a delivery cannula having an internal lumen with an inner diameter;
   b) a graft comprising an annular inflatable ring with an inflation stem for communicating with an interior of the annular inflatable ring, wherein:

the inflation stem has a proximal end and an opposed distal end and has an outer diameter and an inner diameter, and wherein the inflation stem is disposed in the internal lumen of the delivery cannula and includes a duckbill valve; and the inner diameter of the delivery cannula and the outer diameter of the inflation stem are substantially the same, and wherein the graft comprises an annular inflatable graft that defines a hollow cavity when inflated;

c) a release cannula slidably disposed in the delivery cannula, the release cannula having a distal portion configured to engage a proximal portion of the inflation stem; and d) an inflation stylet with at least one internal lumen, the inflation stylet having a distal portion with an outer diameter configured to be releasably press fit into the inflation stem.

* * * * *